United States Patent [19]

Berrebi et al.

[11] 4,296,099

[45] Oct. 20, 1981

[54] PROCESS FOR EXTRACTING EMBRYONIC CALF SKIN AND PHARMACEUTICAL COMPOSITIONS CONTAINING THE SAME

[75] Inventors: Claudine Berrebi; Georges Manoussos, both of Paris, France

[73] Assignee: L'Oreal, Paris, France

[21] Appl. No.: 149,561

[22] Filed: May 13, 1980

Related U.S. Application Data

[63] Continuation of Ser. No. 746,018, Nov. 30, 1976, abandoned.

[51] Int. Cl.$^2$ .......................... A61K 35/48; A61K 7/42
[52] U.S. Cl. ........................... 424/105; 424/DIG. 13; 424/59; 424/359
[58] Field of Search .................. 424/105, DIG. 13, 59

[56] References Cited

U.S. PATENT DOCUMENTS

| | | | |
|---|---|---|---|
| 3,016,334 | 1/1962 | Lewis | 424/359 |
| 3,691,281 | 6/1972 | Battista | 424/359 |
| 3,738,913 | 6/1973 | Johnsen et al. | 424/359 |
| 3,839,590 | 10/1974 | Battista | 424/359 |
| 3,887,703 | 6/1975 | Manoussos | 424/95 |
| 3,991,184 | 11/1976 | Kludas et al. | 424/359 |

OTHER PUBLICATIONS

Kay et al., J. Am. Chem. Soc., vol. 75, No. 16, pp. 4041-4044 (Aug. 1953).
Chemical Abstracts, vol. 68: 33097U (1968) citing Br. Pat. 1,042,007.

*Primary Examiner*—Donald B. Moyer
*Attorney, Agent, or Firm*—Cushman, Darby & Cushman

[57] ABSTRACT

In a process for extracting embryonic calf skin which includes initially grinding the calf skin, extracting the same, separating the resulting extract and lyophilizing the separated extract, the extraction stage is carried out in an extraction medium comprising an aqueous solution having an acid pH, at a temperature between 60°-75° C., for a period of at least 3 hours. The resulting extract which exhibits cicatrisive activity is employed in cosmetic and pharmaceutical compositions.

10 Claims, No Drawings

PROCESS FOR EXTRACTING EMBRYONIC CALF SKIN AND PHARMACEUTICAL COMPOSITIONS CONTAINING THE SAME

This is a continuation, of application Ser. No. 746,018 filed Nov. 30, 1976 now abandoned.

The present invention relates to a process for the extraction of embryonic calf skin and to the use of the resulting extract in the production of cosmetic and pharmaceutical compositions.

Numerous processes heretofore have been proposed for the extraction of proteinaceous tissue and principally tissue from calf skin, these processes generally being effected at a low temperature, either in an acid medium or in an alkaline medium. These mild conditions have been contemplated so as not to alter the extraction product.

However such products are generally obtained only in relatively very small yields and they do not exhibit excellent anti-inflammatory or cicatrisive activity.

It has also previously been proposed to extract certain proteinaceous tissue at very elevated temperatures, for example, temperatures in the order of 90° to 120° C., principally in an aqueous medium buffered at an alkaline pH or also optionally in an acid medium. However, these processes cause degradation of the extraction products which then contain significant amounts of gelatin.

It has now been found that improved extract yields and extracts exhibiting excellent cicatrisive activity can be obtained by effecting the extraction stage of embryonic calf skin, at an acid pH, and within certain critical temperature limits. The resulting extracts are advantageously employed in pharmaceutical and cosmetic compositions.

The present invention thus relates to a process for extracting embryonic calf skin comprising essentially the steps of grinding said embryonic calf skin, extracting the same, separating the extract from the insolubles and lyophilizing said extract wherein the extraction stage is carried out in an aqueous medium at an acid pH and at a temperature between 60° and 75° C. for a period of at least 3 hours.

In a preferred embodiment, the pH of the extraction solution is between about 3 and 5. This pH is obtained by the addition of an organic acid, such as acetic acid, citric acid, trichloroacetic acid, succinic acid, ascorbic acid or lactic acid.

The aqueous extraction solution is employed, generally, in an amount such that the ratio of skin (kg)/liter of solution ranges between 1:1 to 1:4.

Preferably, also, the extraction stage is carried out for a period of time ranging between 3 and 22 hours and more preferably between 8 and 15 hours.

However, heating the extraction medium can be carried out progressively, that is, the extraction medium can be heated for a determined period of time at a temperature lower than 60° C. followed by heating within the temperature limitations specified above.

On the other hand, it is possible initially to heat the extraction medium within the specified temperature limits and then lower the temperature thereof and maintain it at this lower temperature for a varying time.

According to the extraction process of the present invention, it is important that the extraction medium is heated to a temperature between 60°–75° C. for at least 3 hours.

In effect, if the extraction medium is heated at a lower temperature and if the heating is carried out for a time shorter than the specified time limits, an extract is obtained which does not exhibit all the requisite qualities. Moreover the extract yield obtained is considerably smaller.

As indicated above, when the extraction temperature is higher than the specified limits, the extraction products undergo degradation and do not exhibit the desired properties.

It has been established, by tests, that an extraction temperature of 75° C. should be considered as a maximum which should not be exceeded.

Also as indicated above, the proteinaceous tissue employed to carry out the extraction process in accordance with the invention is embryonic calf skin removed between the second month of gestation and birth.

The extraction of the embryonic calf skin can be carried out immediately after removal or the skin can be preserved before extraction; this preservation being effected either by freezing or salting the embryonic skin.

The first stage of the overall process, i.e. the grinding stage is conventional and can be effected dry, principally on frozen embryonic calf skin or in water or even directly in the extraction medium. A typical conventional grinder that can be employed is one known under the commercial name of "Manurkin" or "U-Turrax T.P.".

The separation stage which follows the extraction stage can also be carried out in accordance with conventional methods, that is by centrifugation, by filtration or by drying. This separation stage is generally effected at ambient temperature or at least at a temperature lower than 30° C. In certain instances, it is desirable to repeat the separation stage especially when a centrifugation technique is employed so as to obtain a supernatant which is as clear as possible.

In a situation where the supernatant is slightly colored, it is often desirable to submit it to a complementary decoloration operation using activated charcoal. This supplemental operation can then, if desired, be followed by a centrifugation or filtration technique.

Prior to the final lyophilization stage, it has also been found convenient to concentrate the supernatant under vacuum at a temperature lower than or equal to 30° C., so as to reduce the volume thereof.

The supernatant is then lyophilized by freezing at a temperature between −40° and −60° C., preferably at −50° C.

As a result of the lyophilization, the desired extract is obtained in the form of a cream-white powder which is soluble in water at an acid pH.

The product thus obtained is characterized by the fact that it contains a significant amount of glycine which amount is equal to or greater than three and one half times the amount of hydroxyproline contained therein.

The present invention also relates to cosmetic and pharmaceutical compositions containing the said extract of embryonic calf skin which extract is obtained in accordance with the procedures described above.

The cosmetic composition can be one which is applied topically to human skin and which contains generally from 0.3 to 5 percent by weight of the said extract and preferably from 0.8 to 2 weight percent thereof.

This cosmetic composition can be an aqueous solution having a pH between 4 and 7.

The cosmetic composition, however, can also be provided under other forms such as a lotion, a gel, a cream, an ointment or an aerosol spray.

When the cosmetic composition is applied to the skin, it combats the degradation and ageing of cutaneous tissue; it acts as an anti-inflammatory vis-a-vis redness and burns caused by the sun; and it also favors cicatrization of sores or burns.

The extract of the present invention can also be employed to provide pharmaceutical compositions for parenteral administration, such as intramuscular or subcutaneous injection in a human. These compositions consist essentially of a non-toxic physiologic aqueous solution of an extract produced in accordance with the above described process wherein said extract is present in an amount between 0.5-2 percent by weight thereof, said composition having a pH of about 6.5-7.5 and preferably about 7.

These pharmaceutical compositions, when administered, are very effective against acute or chronic inflammations such as edema or burns, and against subchronic inflammations. These pharmaceutical compositions are also effective in the cicatrization of sores.

The extracts according to the invention can also be employed to produce pharmaceutical compositions to be administered orally to humans which compositions consist essentially of a mixture of a non-toxic ingestible carrier and the embryonic extract produced according to the invention. Such oral compositions can be provided in various forms such as pills, powders, granules, tablets or microcapsules.

To evidence that the extraction temperature and pH conditions are of paramount significance in the attainment of extracts having excellent cicatrisive activity, various comparative tests have been carried out.

To illustrate the influence of temperature on the extraction procedures, the cicatrisive activity of extracts of embryonic calf skin obtained at temperatures between 60°-75° C. have been compared to the said activity of extracts obtained at temperatures either lower or higher than those contemplated by the present invention. These various extractions have been effected in accordance with the procedures of Example 1 below, i.e. at a pH of 4 and with an extraction time of 15 hours.

The results obtained are as follows:

| Extraction temperature | Yield, g/kg of skin | Hydroxyproline mg/g | Cicatrisive activity |
| --- | --- | --- | --- |
| 4° C. | 21 | 3 | 21 |
| 20° C. | 27 | 3 | 18 |
| 40° C. | 90 | 74 | 12 |
| 55° C. | 100 | 92 | 24 |
| 60° C. | 102 | 94 | 30 |
| 65° C. | 105 | 96 | 35 |
| 75° C. | 100 | 95 | 31 |
| 80° C. | 120 | 88 | 17 |
| 90° C. | 105 | 87 | 0 |

Similar tests carried out between 60°-75° C. but using an extraction time of 3 and 22 hours illustrate that the yield and the activity were somewhat smaller relative to the values found above for a 15 hour extraction.

Generally a shorter extraction time while it leads to a slightly smaller yield, also gives a higher activity whereas a longer extraction time provides a better yield, but a slightly lower activity.

It can be seen from the above results that essentially only those extracts produced in accordance with the conditions of the present invention provide extracts having both good cicatrisive activity and an excellent yield.

The extracts obtained at 4° C. and 20° C. while not entirely devoid of cicatrisive activity, their activity is nonetheless considerably weaker than that possessed by the extracts produced at a temperature between 60°-75° C. Further the yield of extracts produced at these low temperatures is very mediocre and it is about 5 times lower than that obtained at the temperatures contemplated by the present invention.

While those extractions carried out at 40° C., 55° C., 80° C. and 90° C. lead to extract yields comparable to those obtained between 60°-75° C., the cicatrisive activity of the lower temperature produced extracts is considerably weaker; for instance, the extract obtained at 90° C. has no recordable activity.

To illustrate the influence of the pH on the extraction procedures, the cicatrisive activity of extracts of embryonic calf skin obtained at temperatures of 60°-75° C. and at a pH 4 have been compared to the said activity of extracts obtained at these same temperatures but at a pH of 8. The extractions have been carried out according to the procedures of Example 1 below except that citric acid has been replaced by a sufficient amount of NaOH to adjust the pH to 8.

The results obtained are tabulated below:

| Extraction temperature | pH | Yield, g/kg of skin | Hydroxyproline mg/g | Cicatrisive activity |
| --- | --- | --- | --- | --- |
| 60° C. | 8 | 70 | 95 | 16 |
| 75° C. | 8 | 70 | 87 | 12 |
| 60° C. | 4 | 102 | 94 | 32 |
| 75° C. | 4 | 100 | 95 | 31 |

It can be seen that the cicatrisive activity of those extracts produced at a pH of 8 is considerably weaker than the activity of the extracts produced at pH 4. The former extracts are about 2-2.5 times less active than those obtained at pH of 4. Furthermore the yields of these higher pH produced extracts are lower.

The cicatrisive activity is a function of the resistance of a scar to be ruptured and is measured in the following manner.

METHOD OF OPERATION

Various groups of animals including at least 10 male Wistar rats each weighing close to 250±10 g were anesthetized with sodium phenobarbitol (50 mg/kg, or 1 ml of a solution of 12 mg/ml). The dorsal area of each rat was then shaved with electric shears.

To study scar rupture strength, wounds are produced by first intention on the shaved dorsal area of each rat by a linear incision of the entire thickness of the skin using a razor blade and scissors. This mediodorsal scar is perpendicular to the axis of the animal and has a length of 1 cm. The edges of the incision automatically touch each other. Thus cicatrization requires neither the use of clamps nor sutures. The animals are then placed in individual cages so as to avoid the disturbance and the contamination of the incision by the other animals.

Thereafter the extract of the present invention was applied to the incision in 5 topical applications, at a rate of 250 mg of cream on a surface of 25 cm², starting J+5 days until J+9 days, J being the day the incision was made.

The animals were sacrificed using chloroform on the 12th day after the incision was made and the following measurements for each were recorded:

(a) the thickness of the skin on all sides of the incision (at 2 cm) using a Lhomargy micrometer; and (b) the scar rupture force using a halter form skin probe, cutting neatly perpendicularly to the axis of the scar.

These skin probes are 1 mm wide and 50 mm long. Their two extremities are fastneed between the jaws of a Lhomargy dynamometer. This exerts a variable pulling force from 0 to 500 g at a constant speed of 5 cm/mn on the scar.

The force required for the rupture of the edges of the scar is recorded by the apparatus in centinewtons. The numbers found are treated statistically by the "t" test of Student.

The percentage of increase of the rupture force of the scar on the animals treated with the composition of the invention relative to those animals not having received any treatment is then calculated.

The following non-limiting examples illustrate the preparation of extracts from embryonic calf skin and several cosmetic and pharmaceutical compositions, in accordance with the present invention.

EXAMPLES OF EXTRACT PREPARATION

EXAMPLE 1

19 kg of fresh embryonic calf skin are ground with 40 liters of distilled water, the pH of which was adjusted to 4 by the addition thereto of the required amount of citric acid.

The resulting extraction medium is then heated to a temperature of 75° C. over night, about 15 hours, at which time the temperature is adjusted to about 35° C.

The extraction medium is then centrifuged at 10,000 rpm for 2 hours at ambient temperature. This centrifugation operation can optionally be repeated if the resulting supernatant is not sufficiently clear. The supernatant is then concentrated under a vacuum at +30° C. and subsequently lyophilized at −50° C.

In accordance with this process, 1.850 kg of the extract of embryonic calf skin are obtained in the form of a powder (100 g of powder per kg of embryonic skin) having a cicatrisive activity of 31. In this example, the citric acid can advantageously be replaced by trichloroacetic acid without lowering either the yield or the cicatrisive activity.

EXAMPLE 2

11 kg of embryonic calf skin are ground in 15 liters of distilled water to which has been added a sufficient amount of acetic acid to impart thereto a pH of 4.

The extraction medium is then heated to a temperature of +60° C. over night (15 hours) at which point the temperature is then reduced to +35° C.

After centrifuging the extraction medium, and treating the resulting supernatant with activated charcoal so as to de-color the same, the supernatant is lyophilized directly without an intervening vacuum concentration. The lyophilization which is carried out at a temperature in the order of −50° C. yields 1 kg of the extract of the embryonic calf skin in the form of a whitish powder (91 g of powder per kg of skin).

In this example, the acetic acid can advantageously be replaced either by succinic acid or ascorbic acid.

EXAMPLE 3

383 kg of fresh embryonic calf skin are ground with 400 liters of distilled water in a Manurkin mill. There is then added sufficient acetic acid so that the extraction medium has a pH of 4.5.

The extraction medium is then heated initially to a temperature of 45° C. for 15 hours and then for 3 hours at 75° C. Thereafter the temperature is permitted to return to about 30° C.

The insolubles are first separated using a clarifier over a 2 or 3 hour period and then the supernatant is treated in a Westalia clarifier for a day. The resulting supernatant obtained is recovered at +4° C. at which point it is all filtered under a vacuum at a temperature of 30° C. on a paper filter using a press. The filtrate is then concentrated on a Thermap concentrator.

1 g of sodium ethylmercurithiosalicylate/5 liters of concentrate is added and the concentrate is lyophilized at a temperature in the order of −50° C., yielding 25 g of extract of embryonic calf skin in the form of a whitish powder (65.5 g of powder per kg of skin).

EXAMPLE 4

300 kg of embryonic calf skin are ground in 400 liters of distilled water, the pH of which has been adjusted to 4 by the addition thereto of a sufficient amount of acetic acid. This extraction medium is then heated to a temperature of 65° C. for 22 hours with agitation. The extraction medium is then centrifuged and clarified as indicated in the preceding examples.

After concentrating the supernatant under a vacuum and lyophilizing the resulting concentrate at −50° C., 30 kg of the extract of embryonic calf skin are obtained in the form of a powder (100 g of powder per kg of skin).

In this example the acetic acid can be replaced by succinic acid without essentially any variation in the yield or the cicatrisive activity.

EXAMPLES OF COMPOSITIONS

EXAMPLE A

A body milk or lotion for treating dry skin, exhibiting redness, is prepared by admixing the following components:

| | |
|---|---|
| Mono- and di-stearate of polyethylene glycol 600 sold under the trade name Tefosse 1500 | 7 g |
| Stearin | 2 g |
| Paraffin oil | 10 g |
| Methyl parahydroxy benzoate | 0.15 g |
| Extract of Example 1 | 0.85 g |
| Sterile, demineralized water, q.s.p. | 100 g |

This body milk when applied regularly to the skin imparts to the skin a satiny and smooth appearance.

EXAMPLE B

A body milk or lotion for application to skin exhibiting redness due to prolonged exposure to the sun and wind is prepared by admixing the following components:

| | |
|---|---|
| Triethanolamine stearate | 7 g |
| Stearin | 2 g |
| Paraffin oil | 10 g |
| Methyl parahydroxy benzoate | 0.15 g |
| Extract of Example 2 | 1.25 g |
| Sterile, demineralized water, q.s.p. | 100 g |

This body milk or lotion when regularly applied to the skin eliminates the redness thereof.

EXAMPLE C

A body milk or lotion for the treatment of scaling leg skin is prepared by admixing the following components:

| | |
|---|---|
| Cetyl alcohol (2%) | 7 g |
| Stearin | 2 g |
| Paraffin oil | 10 g |
| Methyl parahydroxy benzoate | 0.15 g |
| Extract of Example 3 | 0.85 g |
| Sterile, demineralized water, q.s.p. | 100 g |

EXAMPLE D

A cream for treating the neck and face for slight wrinkles or, more particularly, for abused and tired skin, is prepared by admixing the following components:

| | |
|---|---|
| Polyethylene cetyl ether | 2 g |
| Cetyl alcohol | 1 g |
| Stearyl alcohol | 1 g |
| Petrolatum oil | 15 g |
| Lanolin | 3 g |
| Isopropyl palmitate | 5 g |
| Purcellin oil | 3 g |
| Stearic acid | 2 g |
| Carbopol 940 | 0.4 g |
| Triethanolamine | 0.4 g |
| Extract of Example 4 | 1.250 g |
| Methyl parahydroxy benzoate | 0.2 g |
| Sterile, demineralized water, q.s.p. | 100 g |

Daily application of this cream restores to the skin a relaxed appearance and reduces the extent of wrinkling.

EXAMPLE E

A cream for the treatment of blotchiness and slight redness of the skin is prepared by admixing the following components:

| | |
|---|---|
| Polyoxyethylene stearyl ether | 2 g |
| Cetyl alcohol | 2 g |
| Petrolatum oil | 18 g |
| Lanolin | 3 g |
| Isopropyl palmitate | 5 g |
| Stearic acid | 2 g |
| Carbopol 940 | 0.15 g |
| Triethanolamine | 0.4 g |
| Extract of Example 2 | 1.250 g |
| Methyl parahydroxy benzoate | 0.2 g |
| Sterile, demineralized water, q.s.p. | 100 g |

EXAMPLE F

A lotion for the treatment of tired and oily skin is prepared by admixing the following components:

| | |
|---|---|
| Extract of Example 3 | 0.85 g |
| Methyl parahydroxy benzoate | 0.2 g |
| Propylene glycol | 0.5 g |
| Perfume (rose water) | 0.02 g |
| Triethanolamine, q.s.p. pH = 6 | |
| Sterile, demineralized water, q.s.p. | 100 g |

This lotion, applied on the above described skin, imparts thereto a normal and healthy appearance.

EXAMPLE G

A lotion for the treatment of eyelids exhibiting redness and swelling is prepared by admixing the following components:

| | |
|---|---|
| Extract of Example 3 | 0.85 g |
| Methyl parahydroxy benzoate | 0.2 g |
| Glycerin | 0.5 g |
| Perfume (rose water) | 0.02 g |
| Triethanolamine, q.s.p. pH = 6 | |
| Sterile, demineralized water, q.s.p. | 100 g |

EXAMPLE H

An injectable solution is preared by mixing at the time of use 10 mg of the extract of Example 2 with 10 ml of sterilized water. After several injections, an excellent cicatrization of skin exhibiting burns due particularly to prolonged exposure to the sun is noted.

What is claimed is:

1. A process for preparing an embryonic calf skin extract having improved cicatrisive activity from calf skin taken between the second month of gestation and birth comprising the steps of (i) grinding said embryonic calf skin, (ii) extracting the resulting ground embryonic calf skin in an aqueous medium at a pH of 4 obtained by the addition thereto of an organic acid selected from the group consisting of acetic acid, citric acid, trichloroacetic acid, succinic acid, ascorbic acid and lactic acid, the ratio of calf skin, kg/liter of said aqueous extraction medium being between 1:1 to 1:4 and at a temperature between 60° C. and 75° C. for 15 hours, (iii) separating the resulting extract from the insolubles, and (iv) lyophilizing the said separated extract.

2. An extract of embryonic calf skin having improved cicatrisive activity obtained in accordance with the process of claim 1.

3. The extract of claim 2 wherein the amount of glycine contained therein is equal to or greater than 3.5 times the amount of hydroxyproline contained therein.

4. A pharmaceutical composition for parenteral administration to a human to treat acute, chronic or subchronic inflammations and to favor cicatrization of sores comprising in a pharmaceutically acceptable carrier an effective amount of the extract of embryonic calf skin obtained in accordance with the process of claim 1.

5. The pharmaceutical composition of claim 4 wherein said carrier is a non-toxic aqueous physiologic solution and said extract is present in an amount ranging between 0.5 and 2 percent by weight, said composition having a pH of about 6.5 to 7.5.

6. The pharmaceutical composition of claim 5 having a pH of about 7.

7. A composition for topical application to human skin to combat redness, sunburn, degradation and aging of cutaneous tissue and to cicatrize sores or burns comprising in an aqueous carrier applicable to the skin an effective amount of the extract of embryonic calf skin obtained in accordance with the process of claim 1.

8. The composition of claim 7 wherein said extract is present in an amount ranging from 0.3 to 5 percent by weight thereof.

9. The composition of claim 7 wherein said extract is present in an amount ranging from 0.8 to 2 percent by weight thereof.

10. The composition of claim 7 wherein said carrier is an aqueous solution having a pH ranging from about 4 to 7.

* * * * *